(12) United States Patent
Mahon

(10) Patent No.: US 10,565,459 B2
(45) Date of Patent: Feb. 18, 2020

(54) RETROREFLECTIVITY MEASUREMENT SYSTEM

(71) Applicant: Reflective Measurement Systems Ltd, Dublin (IE)

(72) Inventor: James Mahon, Dublin (IE)

(73) Assignee: Reflective Measurement Systems Ltd, Dublin (IE)

( * ) Notice: Subject to any disclaimer, the term of this patent is extended or adjusted under 35 U.S.C. 154(b) by 0 days.

(21) Appl. No.: 16/011,254

(22) Filed: Jun. 18, 2018

(65) Prior Publication Data

US 2019/0163992 A1 May 30, 2019

(30) Foreign Application Priority Data

Nov. 29, 2017 (GB) .................................. 1719823.5

(51) Int. Cl.
*G06K 9/00* (2006.01)
*G01J 1/42* (2006.01)
(Continued)

(52) U.S. Cl.
CPC ........ *G06K 9/00798* (2013.01); *G01J 1/4204* (2013.01); *G01J 1/44* (2013.01);
(Continued)

(58) Field of Classification Search
None
See application file for complete search history.

(56) References Cited

U.S. PATENT DOCUMENTS

| 4,721,389 A * | 1/1988 | Dejaiffe ................. G01N 21/55 |
| | | 356/445 |
| 6,407,674 B1 * | 6/2002 | Gallagher ............ G01M 11/005 |
| | | 340/901 |

(Continued)

FOREIGN PATENT DOCUMENTS

| EP | 1486799 A2 | 12/2004 |
| EP | 1718068 A2 | 11/2006 |

(Continued)

OTHER PUBLICATIONS

Combined Search and Examination Report under Sections 17 and 18(3) for United Kingdom Patent Application No. GB1719823.5, dated May 31, 2018, 8 pages.

(Continued)

*Primary Examiner* — Christopher Braniff
(74) *Attorney, Agent, or Firm* — Withrow & Terranova, P.L.L.C.

(57) ABSTRACT

A retroreflectivity measurement system comprises a light source arranged to project light across a traffic lane during a measurement run, the light being limited to a particular portion of the visible light spectrum. A camera is selectively sensitive to this light to provide first filtered images and separately selectively sensitive to light at a portion of the spectrum not including the particular portion to provide second filtered images. A controller obtains sequences of first and second filtered images during the measurement run, and identifies within the sequences of images an illuminated road marking; determines a first intensity of the marking from a first filtered image, and a further intensity of the marking from the second filtered images; estimates an ambient intensity of the marking, by applying a scaling factor to the further intensity; and determines a retroreflec- (Continued)

tivity of the marking as a function of the first and estimated ambient intensities.

20 Claims, 10 Drawing Sheets

(51) Int. Cl.
*G01N 21/55* (2014.01)
*E01C 23/16* (2006.01)
*G01J 1/44* (2006.01)
*H04N 5/225* (2006.01)
*H04N 5/247* (2006.01)
*H04N 9/04* (2006.01)

(52) U.S. Cl.
CPC .......... *G01N 21/55* (2013.01); *H04N 5/2253* (2013.01); *H04N 5/2256* (2013.01); *H04N 5/247* (2013.01); *H04N 9/04* (2013.01); *B60Y 2400/3015* (2013.01); *G01N 2021/551* (2013.01)

(56) References Cited

U.S. PATENT DOCUMENTS

| | | | |
|---|---|---|---|
| 6,674,878 | B2 | 1/2004 | Retterath et al. |
| 2002/0176605 | A1 | 11/2002 | Stafsudd et al. |
| 2011/0216323 | A1 | 9/2011 | Yoshikawa et al. |
| 2013/0194565 | A1 | 8/2013 | Sørensen et al. |

FOREIGN PATENT DOCUMENTS

| | | |
|---|---|---|
| FR | 2661248 A1 | 10/1991 |
| GB | 2173897 A | 10/1986 |
| GB | 2372314 A | 2/2002 |
| WO | 2011095605 A1 | 8/2011 |
| WO | 2014076324 A1 | 5/2014 |
| WO | 2014096398 A1 | 6/2014 |

OTHER PUBLICATIONS

Extended European Search Report for European Patent Application No. 18177107.2, dated Oct. 8, 2018, 11 pages.

* cited by examiner

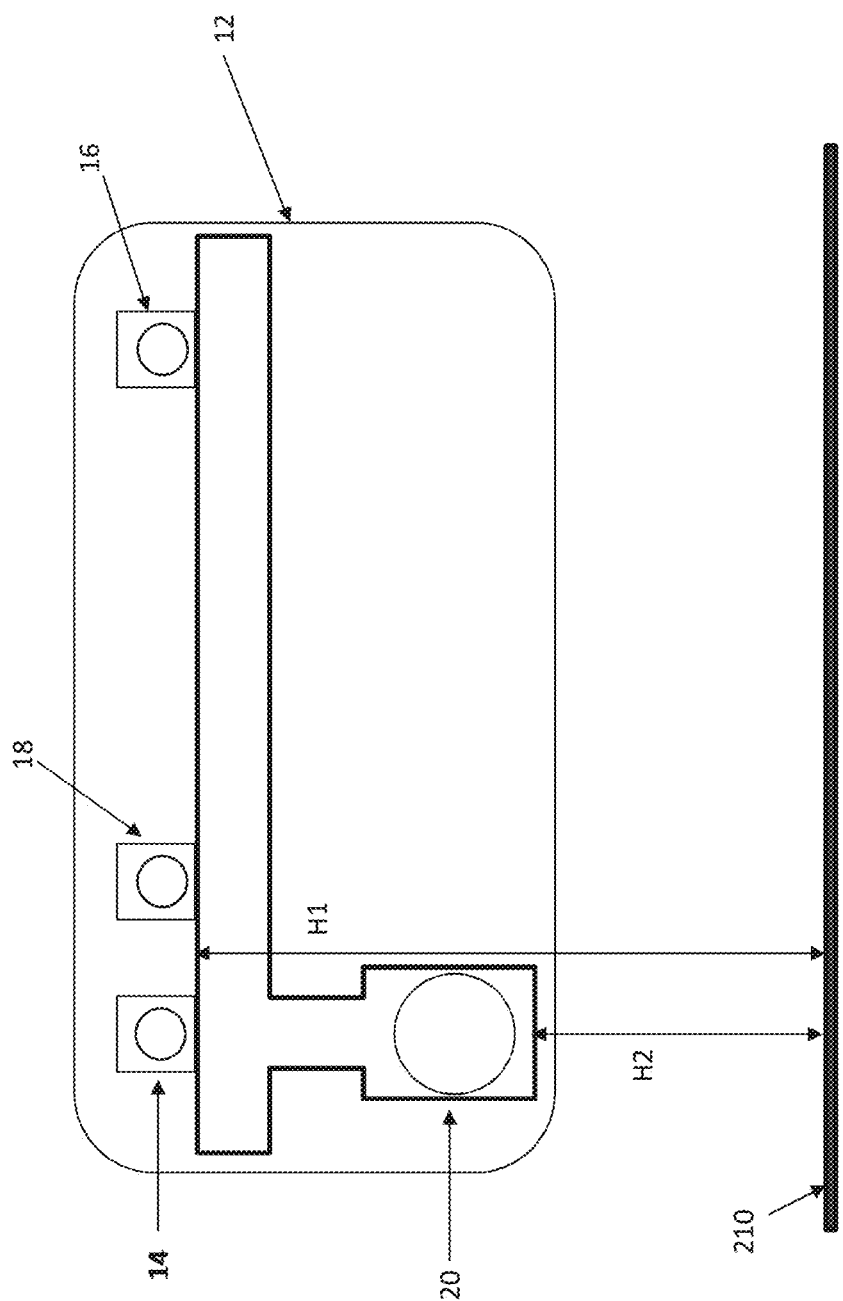

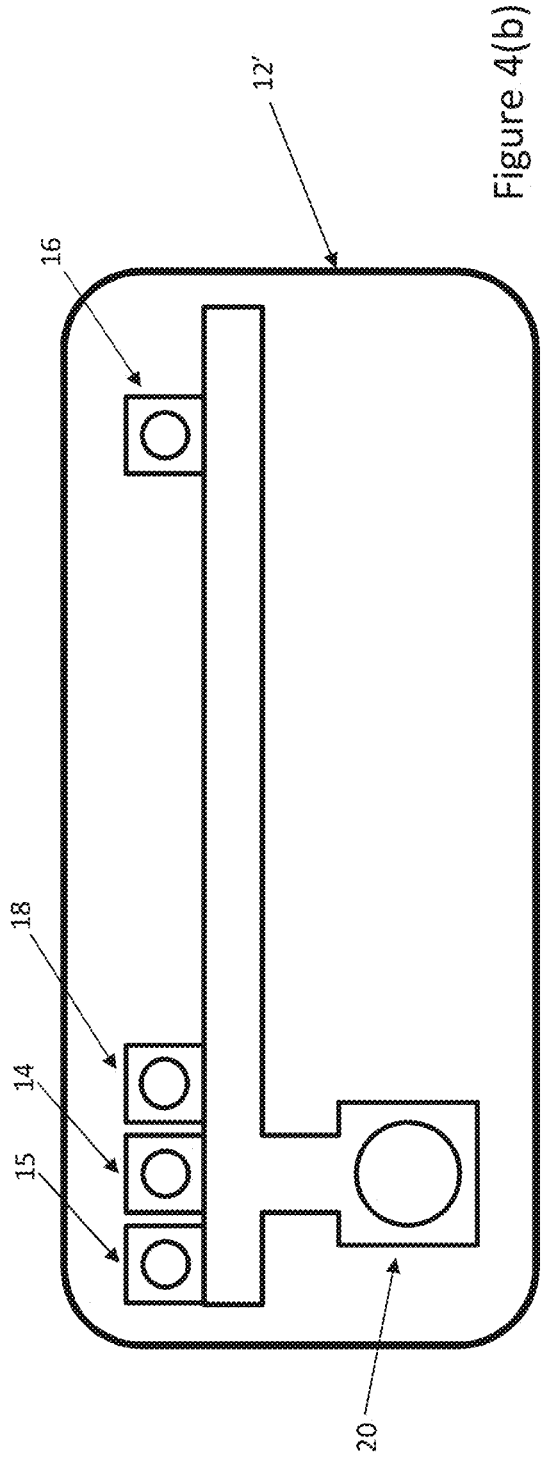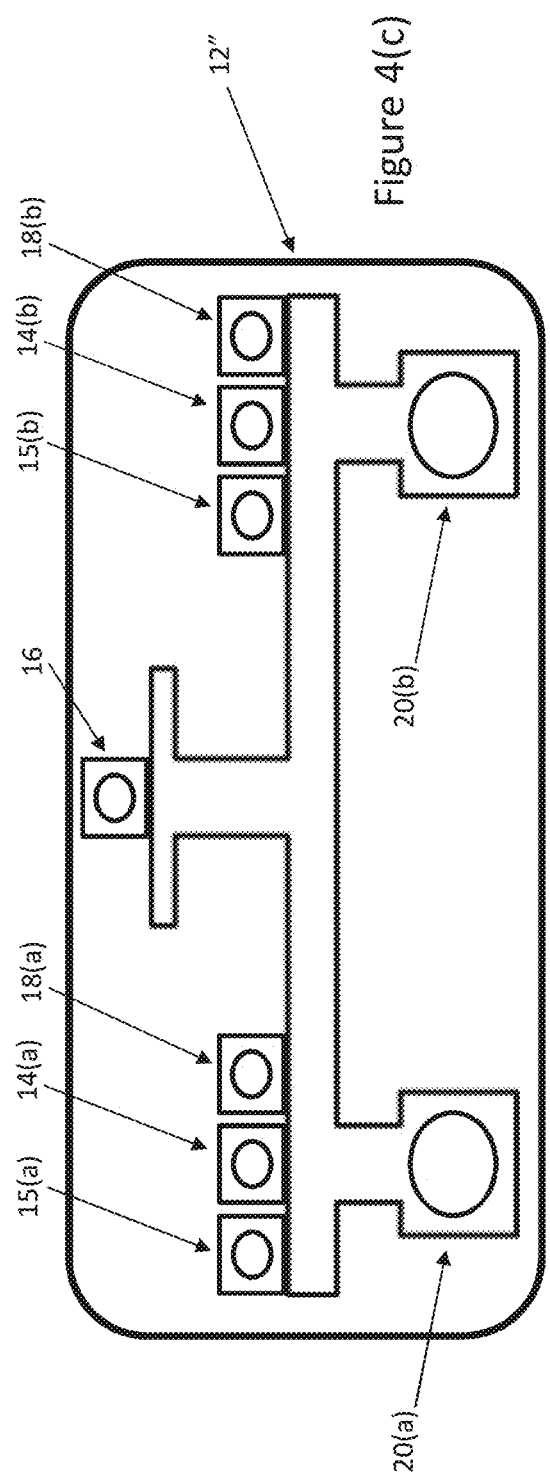

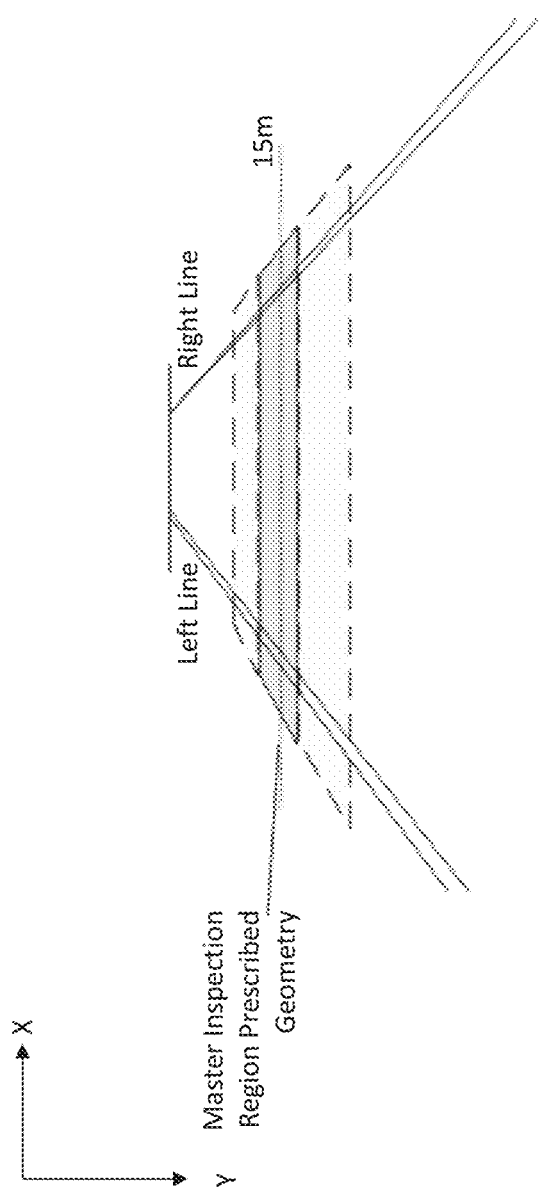

RETROREFLECTIVITY MEASUREMENT SYSTEM

FIELD

The present invention relates to a retroreflectivity measurement system.

BACKGROUND

U.S. Pat. No. 6,407,674, Gallagher discloses a reflectivity measuring apparatus for assessing the integrity of road markings including a light source, a light sensor and a processing means, the apparatus being mounted on a vehicle such that, in use, the light source illuminates a reflective surface on a road marking, and wherein the light sensor detects any reflected light and the data signal is received by the processing means, the processing means processes the data to provide information on the reflectivity of the reflective surface.

U.S. Pat. No. 6,674,878, Retterath discloses a system for the automated determination of retroreflectivity values for reflective surfaces disposed along a roadway. The system repeatedly illuminates an area along the roadway that includes at least one reflective surface using a strobing light source. Multiple light intensity values are measured over a field of view which includes at least a portion of the area illuminated by the light source. A computer processing system is used to identify a portion of the light intensity values associated with a reflective surface and analyse the portion of the light intensity values to determine at least one retroreflectivity value for that reflective surface. In particular, unilluminated images of reflective surfaces are acquired and used as reference images for determining the retroreflectivity value of the reflective surfaces in corresponding illuminated images.

WO2014/096398, Institute Of Technology Blanchardstown discloses multiline retroreflection measurement of road markings using a light source adapted to illuminate the road markings; a first camera adapted to measure the luminance of the road markings; a second camera adapted to make geometrical measurements of the road markings in combination with the first camera; and means for estimating the location of the measured road markings with respect to the first or second camera.

EP1486799 discloses an apparatus comprising an illuminator, a sensor comprising several adjacent detectors, means for controlling the illuminator, and a data processing and control unit. Retroreflection is determined from two photographs taken at substantially the same location. First a photograph is taken without illuminating the target with illuminator. After this, the illuminator is switched on and a second photograph is taken. Retroreflection can also be determined from one photograph, if the illuminator produces a thin strip of light. The luminance is then measured at the point illuminated by the strip of light and above and/or below it.

All of the references discussed above are incorporated herein by reference in their entireties.

SUMMARY

According to the present invention, there is provided a retroreflectivity measurement system comprising a structure arranged to be mounted to a front of a vehicle, the system comprising: at least one light source mounted on said structure and arranged to substantially continuously project light across at least a portion of a traffic lane at a specified distance from the vehicle during a measurement run, the light being limited to a particular portion of the visible light spectrum; a camera apparatus mounted on said structure in spaced apart relationship to said at least one light source and having a field of view including at least a portion of said traffic lane illuminated by said light source during said measurement run, the camera apparatus being selectively sensitive to light at said particular portion of the visible light spectrum to provide first filtered images of at least a portion of said illuminated portion of the traffic lane and said camera apparatus being separately selectively sensitive to light at least at one portion of the spectrum not including said particular portion to provide second filtered images of said illuminated portion of the traffic lane; and a controller arranged to: a) obtain sequences of first and corresponding one or more second filtered images from said camera apparatus during said measurement run; b) identify within at least one of said sequences of images, at least a portion of a road marking illuminated by said light source; c) determine a first intensity of said at least a portion of the road marking from a first filtered image containing said at least a portion of the road marking; d) determine a further intensity of said at least a portion of the road marking from the corresponding one or more second filtered images; e) estimate an ambient intensity of said at least a portion of the road marking within said particular portion of the light spectrum, by applying a scaling factor to said further intensity; and f) determine a retroreflectivity of said at least a portion of the road marking as a function of said first intensity and said estimated ambient intensity.

Embodiments of the system include at least one light source arranged to substantially continuously project light across at least a portion of the traffic lane, wherein the projected light is limited to a particular portion of the visible light spectrum. The system further includes a camera apparatus which is selectively sensitive to light at the particular portion of the visible light spectrum to provide first filtered images of at least a portion of the illuminated traffic lane, and which is separately selectively sensitive to light at least at one portion of the spectrum not including said particular portion to provide second filtered images of the inspected illuminated portion of the traffic lane.

As such, the camera apparatus can provide sequences of first and corresponding one or more second filtered images of the illuminated portion of the traffic lane.

When at least a portion of an illuminated road marking is identified within one of the image sequences by a controller of the system, the controller proceeds by determining a first intensity of the illuminated portion of the road marking from the first filtered image containing such a portion.

The controller also determines a further intensity of the illuminated portion of the road marking from the one or more second filtered images corresponding to the first image and applies a scaling factor to the further intensity (for mapping its intensity value to an expected intensity value within the predetermined spectrum of the source light).

In this way, the system estimates an ambient intensity (i.e. the intensity that would be present in ambient conditions, in absence of the light illumination provided by the system) of the road marking portion falling within the particular portion of the light spectrum used for the measurement illumination, and uses this estimated intensity as reference information in combination to the intensity determined from the first filtered image for calculating the retroreflectivity of the illuminated portion of the road marking.

As such, the system is capable of acquiring a stack of corresponding filtered camera images from which sufficient information can be extracted to obtain direct road marking retroreflectivity measurements, wherein the impact of ambient light is estimated and considered for achieving reliable and accurate measurements.

Notably, this result can be achieved by the system without employing a strobing illumination source. In this way, epileptic (or other strobe light sensitive) people are not affected, especially in cases where the system is used to run the retroreflectivity measurements on a traffic lane during normal traffic conditions.

In some embodiments, the system is arranged to acquire through the apparatus camera the first filtered and corresponding one or more second filtered sequence images substantially at the same time.

Acquiring the first and corresponding first and second filtered sequence images in a single instance of time can avoid or at least limit undesired effects on the retroreflectivity measurement due to the 50 Hz beating of streetlights or to frequency beatings of other light sources illuminating the traffic lane under inspection. Furthermore, the system can run the measurements as fast as the cameras and processing allow, as there is no strobe recharge cycle for the system light source.

In some embodiments, the light projected by the least one system light source is limited to the green light spectrum. In some embodiments, the projected green light matches the photopic response curve of the human eye (i.e. the peak illumination intensity of the green light is substantially at the wavelength corresponding to the peak photopic eye response).

Accordingly, the camera apparatus is selectively sensitive to green light to provide the first filtered images of the illuminated traffic lane; this is advantageous at least because green light can be efficiently filtered, e.g. using a narrowband filter with sharp cut lines, thus improving the rejection of ambient light in the measurements.

The camera apparatus is further separately selectively sensitive to at least one of red light and/or blue light to provide the second filtered images of the illuminated portion of the traffic lane.

Preferably, in scenarios where the system runs retroreflectivity measurements at night time, the camera apparatus is arranged to be selectively sensitive at least to red light. In this way, the ambient intensity of the identified portion of the road marking within the green light spectrum can be accurately estimated, because few red illuminations are expected along the traffic lane during night time conditions (while blue artificial light sources can more frequently appear during the measurement run, e.g. due to some car lights emitting in the blue light spectrum).

In the opposite scenarios, where the system runs the retroreflectivity measurements in day time, the camera apparatus can be arranged to be selectively sensitive at least to blue light. In this way, the ambient intensity of the identified portion of the road marking can be accurately estimated, because less blue light illumination is expected along the traffic lane in daily time than red light illumination (whose amount is also variable dependent on environment conditions, such as the day temperature).

In some embodiments, in order to provide the second filtered images of the inspected illuminated portion of the traffic lane, the camera apparatus is sensitive to light at least at separated first and second portions of the light spectrum which do not include the particular spectrum portion of the system illumination.

As such, the system controller can determine intensities of the identified portion of the road marking from both the corresponding second filtered images in the first and second portions of the light spectrum, and use these intensities to determine a resulting intensity for estimating the road marking ambient intensity.

In this way, the ambient light of the identified portion of the road marking can be more accurately estimated because variations in the light conditions, due to the appearance/disappearance of artificial light sources other than the system light source or to the dependence of the ambient light on environmental conditions, and can be compensated by combining the intensities of the road marking determined at different portions of the light spectrum.

This is particularly effective in scenarios where the system runs the retroreflectivity measurements in day time. Indeed, in these scenarios the ambient intensity of the identified portion of the traffic lane has to be more accurately estimated than during the night period, because the ambient light is brighter and more variable.

In some embodiments, the camera apparatus comprises a single colour camera having a colour filter array CFA (e.g. a Bayer filter) capable of providing both the first and second filtered images. These embodiments minimize the cost and number of components of the system and they are particularly suitable for retroreflective measurements during night time. Indeed, in night time conditions, the ambient light is typically less bright and variable than in the day time; accordingly, the estimation of the ambient intensity of the identified portion of the road marking can be more relaxed than in day light conditions. This means that the filtering for obtaining the first and second images can be smooth (implying a lower amount of light spectrum available for the ambient intensity estimation), while guaranteeing an appropriate accuracy and reliability level for the retroreflectivity measurements.

In some embodiments, the camera apparatus comprises a monochromatic master camera arranged to provide the first filtered images in the particular portion of the light spectrum of the system light source and at least one reference camera arranged to separately provide the corresponding second filtered images.

Using a dedicated master camera for providing the first filtered images means that a narrowband green filter with sharp cut off can be implemented, thus improving the rejection of ambient light in the retroreflectivity measurements.

In these embodiments, the camera apparatus can comprise a single reference camera. For example, in case that the system light source is arranged to project light limited in the green light spectrum, and especially in the scenarios where the retroreflective measurements run during night time, the single reference camera can be a monochromatic camera arranged to be selectively sensitive to red light or to both blue and red light (such as the case of a camera comprising a magenta diachronic filter). Alternatively, the single reference camera can be a colour camera having a colour filter array (e.g. a Bayer filter) arranged to provide both blue and red filtered images.

The use of a single reference camera for providing intensity information of the identified portion of the road marking both in the red and blue portions of the light spectrum can reduce the cost and number of components of the system and it is particularly suitable for retroreflective measurements during night time. Indeed, in night light conditions the filtering for obtaining the second images in the red and blue portions of the light spectrum can be smooth (as the filtering generally provided by an array colour filter or a magenta diachronic filter) while guaranteeing an appropriate accuracy and reliability level for the retroreflectivity measurements.

Especially in the scenarios where the retroreflective measurements run during daily time, the camera apparatus can instead comprise a single monochromatic reference camera arranged to be selectively sensitive to blue light, or a couple of monochromatic reference cameras arranged to be selectively sensitive to blue light and red light, respectively.

In these embodiments, an accurate filtering can be implemented in the red reference camera for sharply cutting off the green and blue portions of the light spectrum; in the latter of these embodiments, accurate filtering can be also implemented in the blue reference camera for sharply cutting off the green and red portions of the light spectrum. This sharp filtering results in a more accurate estimation of the ambient intensity of the identified road marking within the green light spectrum, because it increases the amount of spectrum usable for the estimation.

In some embodiments, especially in scenarios where the retroreflectivity is measured during night time, the system comprises a single light source arranged to project the light on the full width of the traffic lane.

In some embodiments, the system comprises at least a first light source and a second light source mounted in spatial relationship to each other on said structure and arranged so as to illuminate each side of the traffic lane. Theses embodiments are particularly suitable for retroreflectivity measurements running during day time, since the light source has to be much brighter than required for night time measurements (since the ambient light is brighter in day time than at night time).

In some embodiments, the system further comprises at least one stereo camera mounted on said structure in horizontal spaced apart relationship with respect to the camera apparatus. In these embodiments, calibration information relating a horizontal displacement between a feature identified in a first image acquired from the camera apparatus and a second image acquired from the stereo camera to a distance of the identified feature from the vehicle. Preferably, this calibration information relates the distance of the identified feature from the vehicle to a vertical position within an image frame.

Where at least one stereo camera is mounted on said structure in horizontal spaced apart relationship with respect to said camera apparatus; and a memory stores calibration information relating a horizontal displacement between a feature identified in a first image acquired from said camera apparatus and a second image acquired from said stereo camera to a distance of the identified feature from the vehicle, said at least one stereo camera can be selectively sensitive to light at said particular portion of the visible light spectrum to provide third filtered images of said portion of the illuminated traffic lane.

In some embodiments, the stereo camera is also selectively sensitive to light at the particular portion of the visible light spectrum within which the system light is emitted. In this way, the stereo camera can provide third filtered images corresponding to and having intensities similar to those of the first filtered images provided by the camera apparatus, thus simplifying the ranging process.

An angle of said at least one light source can be adjustable so that a structured light pattern is maintained at a distance spanning a particular distance from the vehicle. Preferably, the system is arranged to perform said adjustment either when the vehicle is stationary and/or periodically as the vehicle is moving during a measurement run. Alternatively or in addition, the controller is arranged to detect changes in vehicle pitch relative to the road surface either through analysis of acquired images and/or using a gyroscope. The system can be arranged to adjust said light source either: by adjusting an angle of light projected by the light source; or adjusting a projector pattern position.

The camera apparatus may be arranged to be mounted on said structure above said at least one light source.

The light source may comprise a single light source arranged to project the light on the full width of the traffic lane or the light source may comprise at least a first light source and a second light source mounted in spatial relationship to each other on said structure and arranged so as to illuminate each side of the traffic lane.

The system may further include a positioning device and wherein each determined retroreflectivity is associated with a respective position.

The controller may comprise one or more discrete programmable devices.

The system may comprise an ambient light sensor and be responsive to varying ambient light levels sensed by said ambient light sensor to adjust one of an exposure for said camera apparatus or an intensity of the at least one light source or both to maintain an intensity level for a retroreflective road marking within at least said first filtered images at saturation level.

BRIEF DESCRIPTION OF THE DRAWINGS

Various embodiments of the invention will now be described, by way of example, with reference to the accompanying drawings, in which:

FIG. 4(a) illustrates a front view relative to a road surface of the camera apparatus illustrated in FIG. 3 and of a light source suitable for being used in the system of FIG. 1;

FIGS. 4(b) and 4(c) illustrate variations of the apparatus of FIG. 4(a);

FIG. 5 illustrates a typical field of view for a camera of the system of FIG. 1, showing an illuminated traffic lane region under inspection which contains a couple of road lines;

DESCRIPTION OF THE PREFERRED EMBODIMENTS

Figure 1:
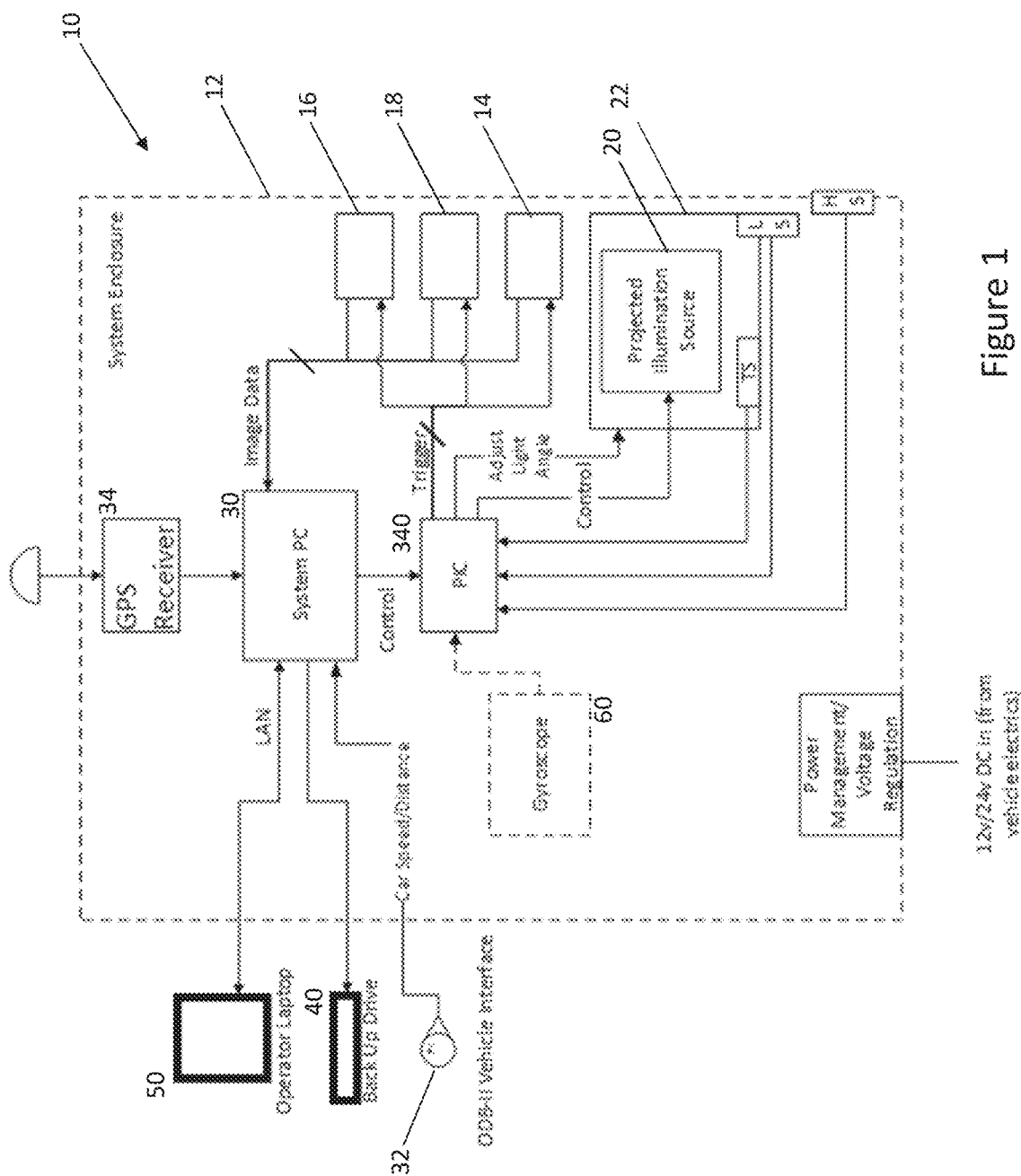
FIG. 1 shows a retroreflectivity system according to an embodiment of the present invention.

Referring now to FIG. 1, there is shown schematically a retroreflectivity measurement system 10 according to an embodiment of the present invention, which is particularly suitable for providing retroreflective measurements at night time.

The system 10 comprises a dedicated enclosure 12 which is arranged to be fitted to the front of a vehicle (not shown). The enclosure 12 includes a light source 20 and an opening for allowing passage therethrough of light from the light source 20 towards the road.

Within the enclosure 12, there are also provided a front facing camera 14 disposed towards a right hand side (when viewed from the vehicle driver's position) of the enclosure 12; a second front facing camera 16 disposed towards the left hand side of the enclosure 12, and a third front facing camera 18 disposed between the cameras 14 and 16, as close as possible to the camera 14.

In the embodiment, the right camera 14 acts as a master camera and as will be explained later, the middle camera 18 acts as a reference camera for estimating a reference ambient light intensity and the left camera 16 acts as a slave, or stereo, camera employed to assist with stereo ranging of detected road features. (Of course, this could be reversed—especially so that the master camera can be located at a driver side of the vehicle.) With reference for example to FIG. 4(a), in order for the right and left camera to be most readily employed for stereo ranging, the cameras 14, 16 are mounted spaced apart within the enclosure 12 at the same height H1 above a road surface 210 i.e. horizontal with respect to one another at a fixed distance apart.

In any case, as illustrated for example in FIG. 4(a), the master camera 14 is vertically aligned with the light source 20 within the enclosure 12 to comply with relevant standards requirements, such as the EN1436 standards.

Figure 2:
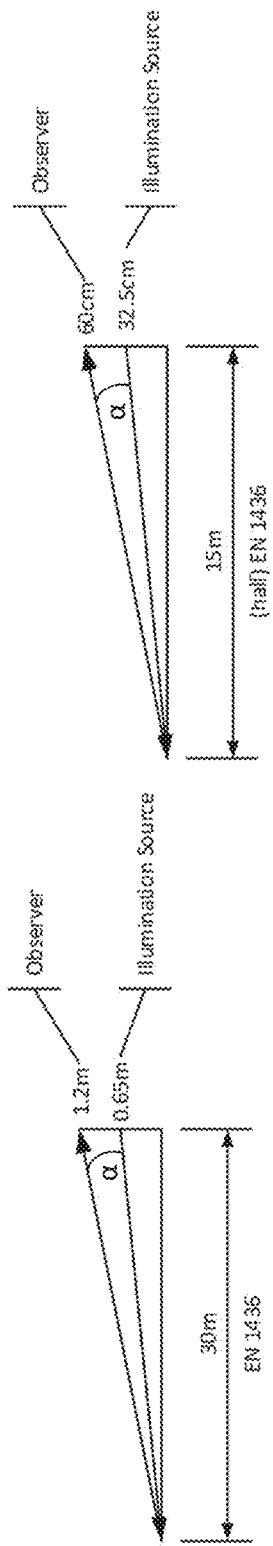
FIG. 2 shows the prescribed geometry for the American Standard ASTM E 1710 and the equivalent European Standard EN1436, and the geometry scaled down by ½.

Referring now to FIG. 2, European Standard for Road Markings EN 1436 specifies an angle α between an illumination source and observer when measuring retroreflectivity. While the exemplar provided in the standard indicates a measurement distance of 30 m in front of a vehicle, it is permissible to make measurements at a distance of 15 m from the vehicle, but preserving the geometry and scaling heights and ranges accordingly. It will also be appreciated that while in the exemplar provided in the standard, as in FIG. 2, as well as in FIGS. 3 and 4(a), the observer, i.e. the master camera 14, is shown located above the illumination source 20, it is also permissible to locate the illumination source 20 above the observer. Thus, with reference to FIG. 4(a), in some embodiments of the present invention the right-master camera 14 is located within the enclosure 12 at a height H1 of 0.325 m above the road surface 210 and the light source 20 is centred above the master camera 14 at a height H2 of 0.60 m above the road surface 210.

In alternative embodiments of the invention, a dedicated master camera located below the light source 20 could be employed along with separate left and right stereo ranging cameras located on either side of the light source 20.

It will be appreciated that the same arrangements can be employed to meet the American Standard ASTM E 1710.

Referring to FIG. 5, there is illustrated a typical field of view of the master camera 14. The light source 20 is arranged to project a slot of light extending across a traffic lane in an X direction, horizontal and transverse to the direction of vehicle travel, typically about 6 m wide, from about 13 to 16.5 metres (typically at 15 metres) ahead of the vehicle to which the enclosure 12 is mounted (e.g. as requested by the EN1436 geometry).

This region is referred to as the master inspection region. Note that in the present specification, the vertical direction in the field of view of the camera is referred to as the Y direction, with the origin X=0, Y=0 at the top-left of the field of view.

Figure 3:
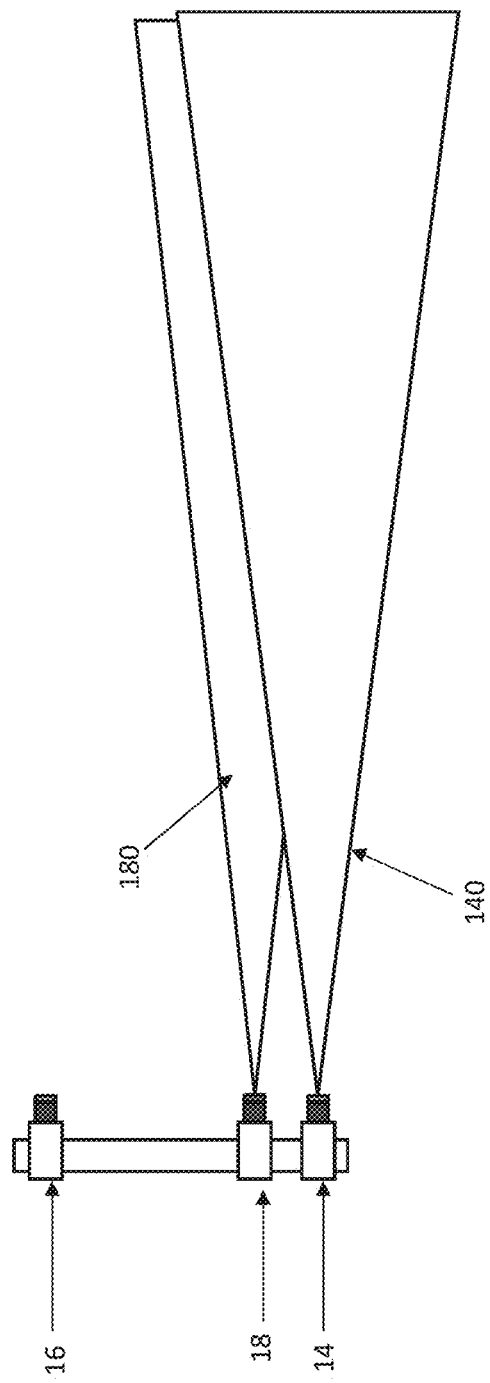
FIG. 3 illustrates a plan view showing a camera apparatus of the system illustrated in the system of FIG. 1.

With reference to FIG. 3, the reference camera 18 is disposed in the enclosure 12 so that its field of view 180 overlaps as much as possible the field of view 140 of the master camera 14 to include at least a portion of the master reference region where road marks are expected to appear while the vehicle is travelling along the road.

The light source 20 illuminates the road surface constantly as the vehicle conducts a measurement run along a section of road to be tested.

The light projected by the source 20 is monochrome green light, i.e. light limited to the green portion of the light spectrum (e.g. comprising approximately a wavelength range between 495 and 570 nm). In particular, the green light is emitted by the source 20 so as to match the photopic response curve (V lambda curve) of the human eye which is illustrated for example and indicated with numeral reference 200 in FIG. 6. In practice, the peak illumination intensity of the projected light is substantially at or as close as possible to the wavelength corresponding to the peak of photopic eye response (having a value of about 555 nm).

Preferably, the light source 20 comprises a LED source which could include one or an array of green LEDs. This LED source 20 is capable of providing a required bright illumination with a low etendue. The use of LED technology can efficiently contain the power consumed for illumination and, therefore, the heat generated in the system 10. In order to dissipate the generated heat, the system 10 can comprises an active cooling system (not shown). It will also be appreciated that in some implementations it could be useful to further filter the light source 20 to reduce the amount of light spreading out into Red and/or Blue regions of the spectrum.

In some embodiments of the invention, the entire light source 20 can be moved through a limited vertical range of said ±1 mm, so that all the light from the light source 20 reaches the master inspection region. In still further alternative implementations, the light from the light source can be projected through an optical light guide. In any of these cases, as will be explained in more detail below, the projected image can be adjusted, or the light source or light guide can be moveably mounted through a limited vertical range to allow the position of the projected light on the road surface 210 to be adjusted, for example, to take into account different loading of the vehicle, undulations in a road surface or acceleration/deceleration of the vehicle and so to light the master inspection region of the road at the required distance from the vehicle.

Referring back to FIG. 1, in order to assist in maintaining a constant intensity output from the light source 20, a number of sensors can be provided within or on the enclosure 12. A temperature sensor TS can measure the temperature within the enclosure 12, at the region housing the source 20. For example, if the light source 20 were to heat beyond an operating threshold, its output light intensity would reduce. To prevent this, the system 10 attempts to keep the temperature within the enclosure limited to the operating limits of the light source 20 by actuating active cooling or other measures (not shown) in response to temperature measurements from the sensor TS. A humidity sensor HS can also be provided, and this enables a humidity measurement to be stored with retroreflectivity results. In some embodiments, the humidity sensor could allow the power of the light source 20 to be adjusted to compensate for varying environmental humidity which would effect retroreflectivity measurements. The humidity sensor also enables a dew point to be estimated. Finally, a light sensor LS is provided so that the light intensity at the light source 20 within the enclosure 12 can be measured. The system can thus record the intensity of the light source 20 both at calibration, prior to a measurement run, and when the system is inspecting, during a measurement run, so that an operational measured intensity and the calibrated intensity can be used to compensate for an increase or decrease in operational intensity relative to the calibration intensity.

Each of the sensors TS, HS, LS are connected to a PIC (Peripheral Interface Controller) controller 340. Of course, in variants of the embodiment, equivalent controllers can be employed. The PIC controller 340 in turn controls the light source 20 as required; and also the PIC controller 340 can be used to control the angle of the projected light beam by varying the projected image or light guide (when present) within the enclosure 12 as mentioned above.

Figure 6:
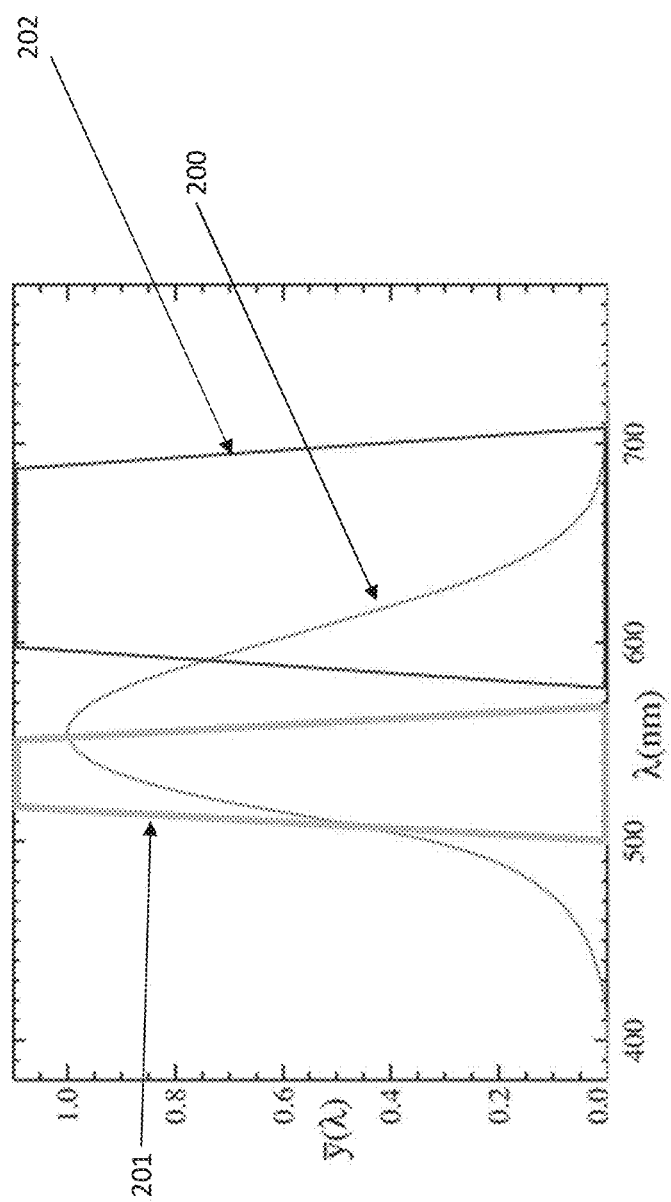
FIG. 6 illustrates a light frequency diagram showing the green narrowband filter and the red bandpass filter of the master camera and reference camera, respectively, of the system illustrated in FIG. 1, together with a photopic response of the human eye.

With reference to FIG. 6, the master camera 14 is arranged to apply a narrowband green filter 201 to incoming light, defined by sharp edges and having a bandpass allowing the passage of the green light emitted by the illumination source 20. For example, the green filter 201 illustrated in FIG. 6 has a bandpass delimited by cut-off frequencies of about 520 nm and 550 nm.

The filter 201 can be physically implemented by disposing one or more green optical filters at or close to the lens of the master camera 14, or over or close to the image sensor of the camera 14, so as to filter incoming light before it can reach the image sensor. Alternatively, the filter 201 can be implemented by configuring the image sensor itself, for example, through suitable choice of materials, to selectively convert an electrical signal only in response to incident green light.

As such, the master camera 14 acts as monochrome camera arranged to provide first green filtered images of road portions illuminated by the green light source 20 in the master reference region, while the vehicle is travelling along the road for running the retroreflectivity measurements.

Preferably, the stereo camera 16 is arranged to provide the same green narrowband filter 201 as the master camera 14 so as to generate, in response to incoming green light, filtered images corresponding to and having intensities similar to those of the green filtered images provided by the master camera 14. In this way, the ranging process using the information provided by the master and stereo cameras 14, 16 is simplified.

With reference again to FIG. 6, the reference camera 18 is arranged to apply a bandpass red filter 202 to incoming light, having sharp edges and a bandpass allowing the passage of incoming light within at least a portion of the red visible light spectrum. For example, the red filter 202 illustrated in FIG. 6 has a bandpass delimited by cut-off frequencies approximately between 600 nm and 690 nm. Clearly, it is desirable where possible to provide filters which are as narrow as possible, for example, as narrow as 20 nm, and as close together as possible.

Again, the filter 202 can be physically implemented by disposing one or more red optical filters at or close to the lens of the master camera 14, or over or close to the image sensor of the camera 14, so as to filter incoming light before it can reach the image sensor. Alternatively, the filter 202 can be implemented by configuring the image sensor itself, for example, through suitable choice of materials, to selectively convert an electrical signal only in response to incident visible red light.

As such, the reference camera 18 acts as a monochrome camera arranged to provide second red filtered images of the illuminated road portions falling within the master reference region, while the vehicle is travelling along the road for running the retroreflectivity measurements.

With now reference back to FIG. 1, the PIC controller 340 is also connected to each of the system cameras 14, 16, 18 and causes each camera to acquire and provide a respective filtered image when required. For example, the PIC controller 340 can synchronise the system image acquisitions through the cameras 14, 16, 18 in such a way that these acquisitions occur at the same time instance, with an acquisition frequency preferable between 10-40 Hz.

The PIC controller 340 is in turn controlled by a central system controller 30, in this case, a conventional type general purpose computer. The central controller 30 can communicate with the vehicle control system (not shown) through for example, its ODB-II vehicle interface 32 to obtain for example, the car speed and distance travelled from the vehicle as well as any other vehicle information, such as whether its headlights are on or not or dipped. Although in some embodiments, images are captured at a constant rate, vehicle speed information enables the central controller 30 to determine a variable rate at which images can be captured by the cameras 14, 16, 18.

In addition or as an alternative to the ODB-II vehicle interface 32, the central controller 30 can also connect to a GPS receiver 34 to determine the vehicle's location, so that each or some of the camera image acquired from the cameras 14, 16, 18 can be tagged with GPS information synchronized with their acquisition time.

Once triggered by the PIC controller 340 in accordance with the instructions of the central controller 30, each of the cameras 14, 16 and 18 provide the captured filtered images to the central controller 30. In this way, the system 10 is capable of obtaining sequences of filtered images, each comprising a filtered image provided by the master camera 14 and corresponding filtered images provided by the reference camera 18 and the stereo camera 16. These sequences of images can be offloaded to a back-up drive 40; and/or a separate computer 50 for further processing, analysis, review or archiving as required. As such, at each triggering time instance, the system 10 can acquire the corresponding filtered images from the cameras 14, 16 and 18 as well as GPS readings (north and East etc.) tagged with one or more of these images.

In a typical example, the system 10 acquires, in a synchronous way from each camera 14, 16, 18, 10-20 images/second during a measurement run with the vehicle moving at speeds of 27 m/sec to ensure overlap of illuminated image regions from image frame to frame and so to enable measurement of retroreflectivity for a complete road marking. (Measurement runs are expected to take place while the vehicle carrying the system 10 is travelling at normal road speeds (from 50-75 mph, typically 60 mph or 100 kph for instance).) For example, at 20 frames per second, each point on a road can be inspected twice with a 3 m deep master inspection region. Each frame is typically a 2 ms exposure, which is fast enough to stop motion blur and long enough to get as much light as required for inspection.

Before beginning measurement runs, a system precalibration process is performed. The precalibration process employs (in a controlled environment) a white light source, suitable for simulating ambient light in typical conditions where the system 10 conducts measurement runs. The white light source is used for illuminating a white object, such as a clean diffuse white board having a width of about 7 m.

A first measurement of the intensity of the white object is performed, where the white light is masked before reaching the white object so as to remove at least its components within the green light spectrum A second measurement of the intensity of the white object is performed where instead the white light is filtered to be limited to the green light spectrum.

The corresponding intensities acquired during the first and second measurements can be used to calculate scaling factors for mapping intensity values of an object determined from images outside the green light spectrum to expected intensity values of the object within the green light spectrum.

For example, by applying in the first measurement a bandpass red filter to the white light (for cutting-off its blue and green spectrum components), at least one scaling factor can be calculated for mapping intensity values of an object determined from acquired red images to expected intensity values of the object within the green light spectrum.

Analogously, by applying in the first measurement a bandpass blue filter to the white light (for cutting-off its red and green components), at least one scaling factor can be calculated for mapping intensity values of an object determined from acquired blue images to expected intensity values of the object within the green light spectrum.

The calculated scaling factors are stored in the system 10 for subsequent use during the measurement run as will be disclosed later. Alternatively, the intensity values from the first and second precalibration measurement runs are stored in the system 10, and when needed during the measurements, the system 10 retrieves these values for calculating the necessary scaling factors.

A number of other different types of system calibration can be performed. For example, the light source 20 can be calibrated across the X direction of its projected field. While the light source 20 should ideally project an even illumination field across the fields of view 140, 180 of the cameras 14, 16 and 18, it is typically not perfect. To compensate for variation in illumination across the field of view, an illumination profile comprising a look-up table or equivalent function PIV (Position in View) for the light source 20 can be determined by projecting light from the light source 20 onto a uniform surface such as a clean diffuse white board (in a controlled environment with no ambient lighting). The measured intensity can then be used to build the look-up table or the parameters for the function PIV, so that at runtime, a measured intensity I at any position x within the field of view can be adjusted to provide an adjusted value I'(x) as follows: I'(x)=PIV(I,x). The calibration to provide PIV can be performed during system construction and installation, but can also be verified/updated at any time (if a white board or equivalent is available).

Figure 7:
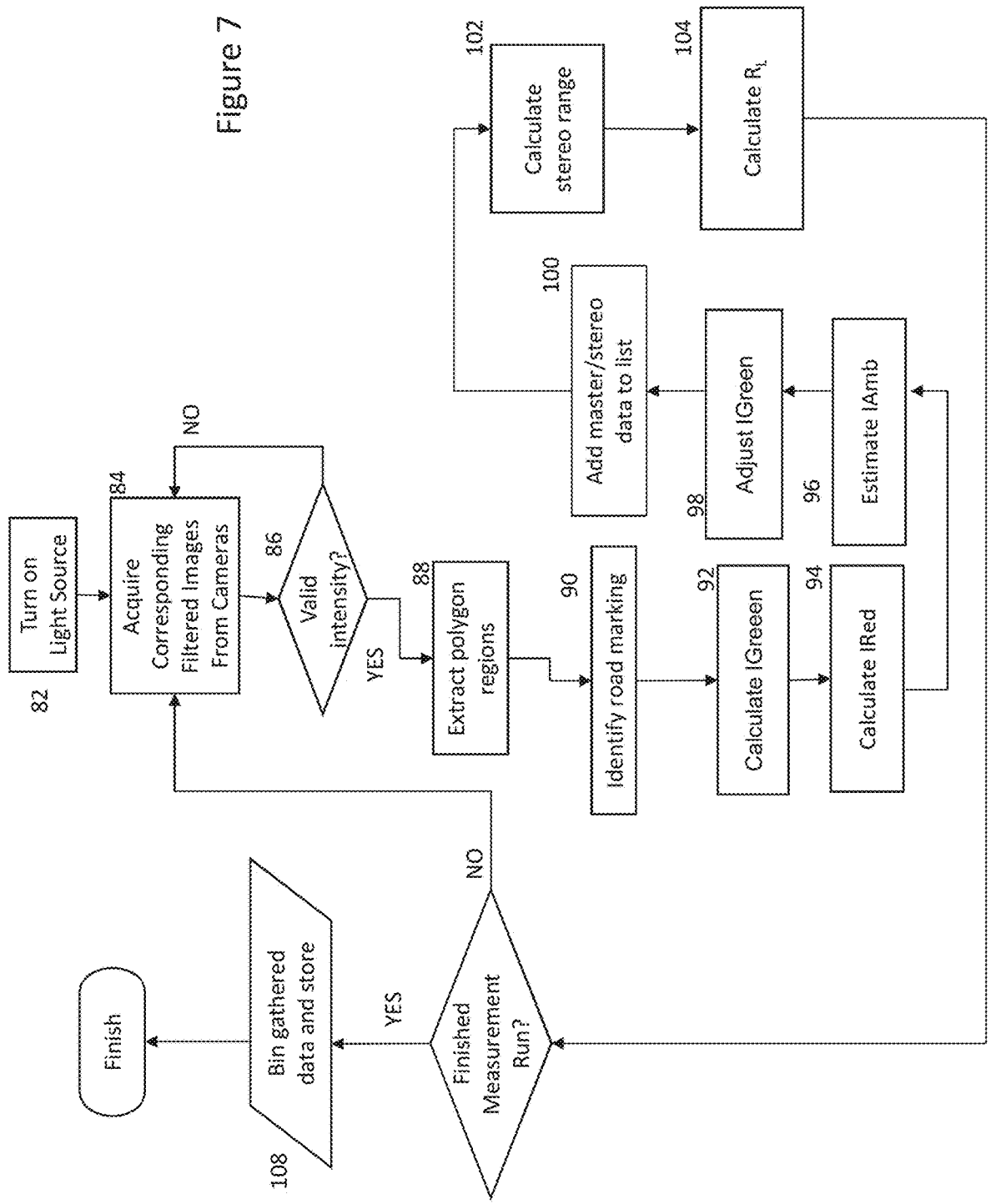
FIG. 7 illustrates the operation of the system of FIG. 1 during a measurement run.

Referring now to FIG. 7 which describes the steps of a typical measurement run, the light source 20 then turned on, step 82, and remains on for the duration of a measurement run so as to substantially continuously project green light on the road surface.

The system 10 now begins to loop and at each iteration of the loop acquires a set of corresponding filtered images provided by the cameras 14, 16, 18 (step 84), in order to track and measure the retroreflectivity of road markings within the field of view of the cameras.

The system 10, first tests if the mean intensity of each acquired filtered image is within a set range, step 86. If the mean intensity is too high, the set of images are discarded and the system reverts to acquiring another set of images. This mitigates problems caused by the cameras 14, 16, 18 blooming out due to oncoming traffic, or being too close to a preceding vehicle. In addition, using the ODB-II vehicle interface 32, gyroscope 60 or GPS receiver 34, the system 10 can determine if the vehicle is turning and so can avoid processing images when the turn angle is too great, for instance on corners and roundabouts. (In some embodiments the gyroscope 60 can be incorporated within the GPS receiver 34; or indeed both the gyroscope 60 and GPS receiver 34 could be incorporated within an automotive navigation system.)

In case of determining a valid intensity at step 86, the system 10 proceeds by attempting to identify at least a portion of a road marking within at least the filtered green image provided by the master camera 14.

For example, at step 88, the system 10 defines a respective polygon surrounding the expected location of any illuminated road marking being tracked at each of the left and right sides of the green filtered image provided by the master camera 14. As such, each side of the scene is processed separately. The position of the polygon is updated based on the locations of the lines within the last N frames (N typically 16).

Figure 8:
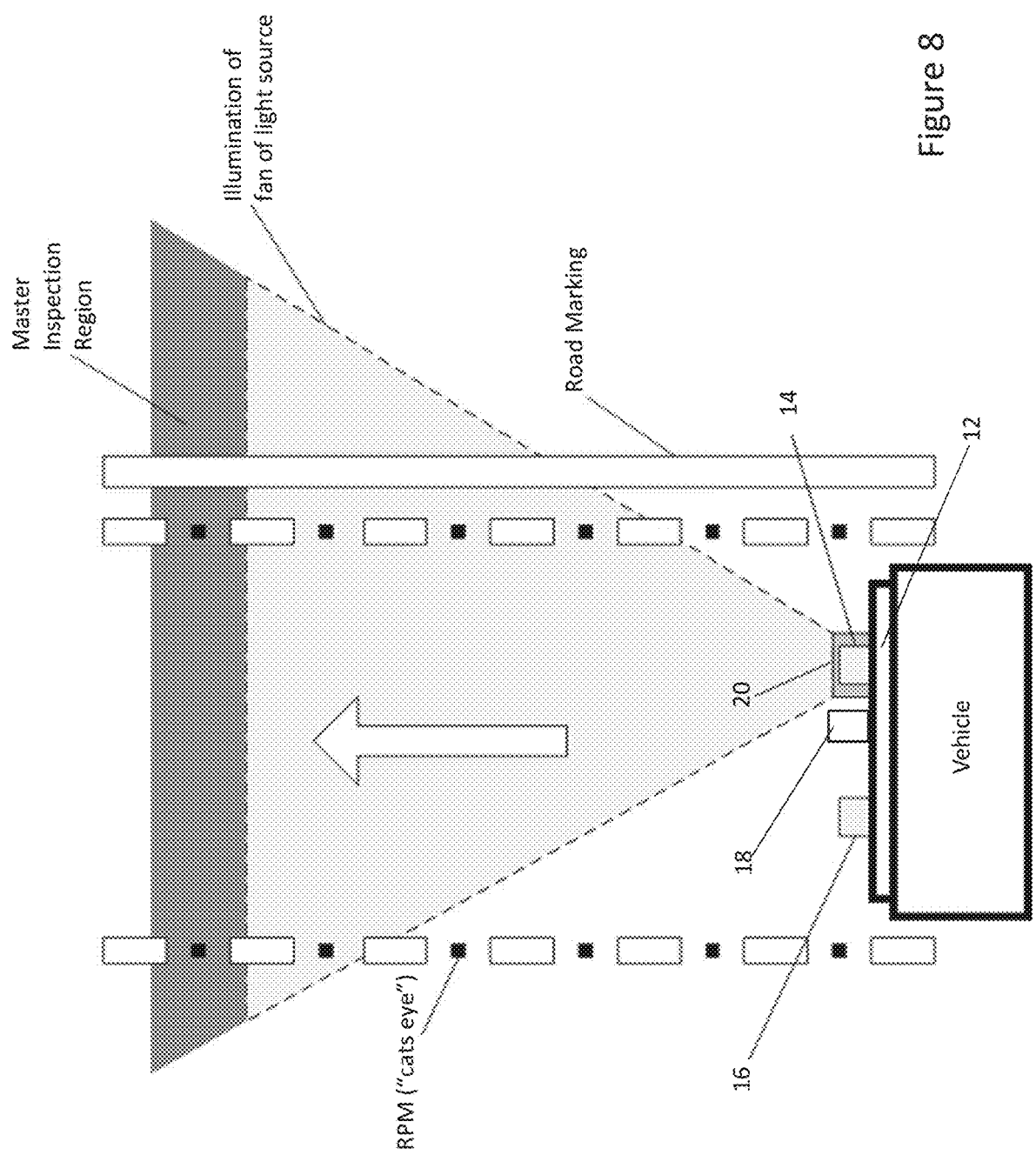
FIG. 8 shows a light source and measured road features.

Referring to FIG. 8, it will be seen that the system 10 can be attempting to track the intensity of a number of road markings at any given time. In this example, there is a solid continuous road marking towards the right hand side of the field of view, along with a parallel broken line and a broken line towards the left hand side of the field of view. It will be noted that in this case, there are RPMs (cat's eyes) located in the gaps between the broken lines. As will be explained below, reflected light from RPMs will typically produce saturated regions within the acquired images and these regions are filtered out for the purposes of determining the retroreflectivity of the road markings. So for example, any pixel with an intensity greater than 240 (out of 255) is discarded or ignored during the processing for road markings.

Figure 9:
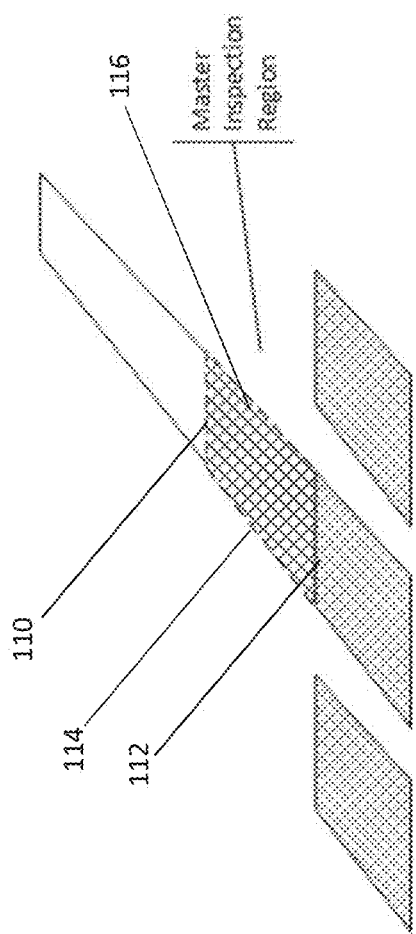
FIG. 9 illustrates checking if a reference region coincides with a road marking or a road surface.

Referring now to FIG. 9, in one implementation, the system 10 fixes two horizontal lines 110, 112 at pre-defined Y positions, each with given widths within the image, the first line 110 corresponding to a leading edge of the master inspection region and the second line 112 corresponding to a trailing edge of the master inspection region. These lines need to be spaced apart sufficiently in the Y direction to ensure an overlap of analysed regions from one image frame to the next, but ideally should lie within the illuminated region of the road surface. The second line 112 may be wider than the first 110 and the lines need to be wide enough to ensure that a polygon comprising the lines 110, 112 and lines 114, 116 connecting the ends of the line 110 to the corresponding ends of the line 112 will surround a road marking being tracked.

The system 10 centres each line 110, 112 around an expected road marking position. This expected road marking position can be tracked from frame to frame with the lines 110, 112 being centred about the centre of a road marking detected in a previous frame. It will be appreciated that the process is repeated for each road marking being tracked and so in the example of FIGS. 5 and 8, polygons will be defined for the master inspection region, one for each road marking. In some embodiments, the polygons for the first image frame can be defined manually, automatically, through image feature analysis, or semi-automatically through operator adjustment of automatically detected features. Once polygons which are expected to surround each road marking being tracked are defined, the system 10 can then proceed to identify road markings within each polygon. Using polygons in this fashion reduces the area to be inspected and so and makes analysis faster; also, reducing the analysis area as much as possible excludes spurious objects which might be detected as road markings or RPMs.

In step 90, a grey level threshold is generated for the image region inside each polygon using, for example, histogram analysis. Using this threshold, the system attempts to locate any contiguous regions of pixels above the threshold intensity—any number of conventional techniques are available to do so. These bright regions are assumed to correspond to respective portions of a road marking illuminated by the system 10 and it will be appreciated that for a broken line road marking such as those shown in FIG. 8 (or a poorly maintained road marking) more than one bright region per polygon may be detected. As such, the image is thresholded to enable a line or other road marking to be detected as a binary image, as the line or other road marking is expected to be much brighter than the road material.

For each bright region detected in the green filtered sequence provided by the master camera 14, an intensity value $I_{Green}$ is calculated at step 92.

At step 94, an intensity value $I_{Red}$ is also calculated for a region in the corresponding red filtered image provided by the reference camera 18, spatially corresponding to the detected bright region in the green-filtered image.

At step 96, the system 10 estimates an ambient intensity $I_{Amb}$ of the identified region within the green light spectrum, by applying a suitable scaling factor to $I_{Red}$, for mapping the $I_{Red}$ value to a value expected in the green light spectrum. The scaling factor is that calculated and stored in the system 10 during the pre-calibration process, as disclosed above.

At step 98, the system 10 adjusts the calculated $I_{Green}$ by subtracting therefrom the estimated $I_{Amb}$. As such, the system 10 compensates the effect of the ambient light (i.e. the light other than that projected from the system source 20) on the determination of $I_{Green}$, where green ambient light can be allowed to pass by the filter 201 as well as the green light projected by the system source 20.

Optionally, the calculated $I_{Green}$ could be further adjusted for its X position in the field of view using the PIV(I, x) table/function explained above, when available to the system 10 from a calibration process performed before turning on the light source 20. A Y value can be determined for the identified bright region and for example, can be chosen as midway along the length of a region or chosen as a Y value dividing a region into two equal numbers of pixels. The values for each bright region detected within a polygon can be aggregated or each region's values can be maintained separately, but in any case, for each polygon, an adjusted intensity value of $I_{Green}$ can be provided. In some implementations, if a bright region is too large in the Y direction, it can be divided into two or more sub regions, each processed as a separate line segment. For each segment, the Y position chosen is the centre of the line segment in the Y direction.

As explained above, the road marking identified within the filtered green image provided by the master camera 14 would be also located in the filtered green image provided by the stereo camera 16, and the disparity between the two is used to calculate the range to the line or other road marking at this point.

The system 10 can now add the data from the green-filtered images provided by the master and stereo cameras 14, 16 to a list (step 100), and repeat this process for the image frame acquired from the stereo camera 16. This processing should produce the same bright regions as detected for the master camera 14, but with each feature detected in the green filtered image provided by the master camera 14 shifted in the X direction relative to the same feature detected in the corresponding green filtered sequence image provided by the stereo camera 16.

At step 102, the system determines the X, displacement between detected bright regions in the master inspection region at the determined $Y_m$ position. Knowing the $X_m$ displacements, the system 10 now knows in metres the range of the master positions from the system 10.

At step 104, knowing the adjusted intensity $I_{Green}$ of the green light reflecting from the identified road marking, the range to the marking points r, and the intensity of the green light projected by the light source 20 at this position on the road marking, the system 10 is capable of calculating the retroreflectivity $R_L$ of the road marking, according to the equation:

$$R_l = [I_{Green}] r^2 C_{rl}$$

where $C_{rl}$ is a scaling factor determined by training the system with an object of known retroreflectivity under normal operating conditions i.e. light source 20 on and headlights on. (In some cases a pair of scaling factors ($C_{rl}$) can be defined both for headlights on low beam (dipped) and on main beam.)

The process from step 84 to 104 is then repeated for successive sets of filtered images provided by the cameras 14, 16, 18, until a measurement run is completed.

When the measurement run is completed, at step 108, for each road marking inspected and measured along a section of road, the system can store $R_l$, GPS coordinates, inspected image intensity values etc. for later review, analysis and/or reporting. Where a GPS coordinate is not available at a given time, for example, if the vehicle is in a tunnel, the system can use actual vehicle speed and distance travelled, obtained via the OBD-II interface 32, to interpolate between GPS measurements and to provide an estimate of vehicle location for any given $R_L$ measurement. Alternatively, the GPS receiver 34, if it includes automotive dead reckoning (ADR), may be able to provide this directly. In this case, the GPS receiver 34 can communicate directly with the ODB-II interface 32 to obtain distance and velocity information from the vehicle.

It will be appreciated, however, that while the system 10 can record data for every measured line segment, for the purposes of line maintenance, this may not be very actionable. As such, the system can be set up to aggregate data recorded for segments of typically 100 m. The measured $R_l$ data can thus be filtered for noise (for instance) by sorting the data, excluding outlying measurements and deriving an average or median $R_l$ for the segment for subsequent storage. A line coverage metric (with respect to expected line coverage) can also be calculated and stored for each segment. Other information such as an average detected width (in centimetres) for the road marking within the road segment; or an average contrast measurement as between the road marking and the road surface for the road segment can also be stored.

The stored information for road lines, signs RPMs etc. can be retrieved and displayed in any suitable fashion by a user. For example, a user could interact with a map to determine retroreflectivity measurements or quality for a specific location, for a selected length of road or even a selected area of a map.

It is also appreciated that the vehicle to which the system 10 is mounted is subjected to motions, vibrations and changes in road profile. These changes can either be slow, for example, due to changes in vehicle loading, or faster where the vehicle tilts and pitches due to acceleration, deceleration and changes in road surface or vehicle balance while driving.

To generate reliable and accurate retroreflectivity measurements $R_l$, the prescribed geometry of the illuminated inspection region on the road surface relative to the vehicle should be maintained, especially for the ranging calculations described above.

As mentioned above, the light source 20 can be adjusted to compensate for changes in vehicle orientation relative to the road by changing the angle of the projected light beam. This can be done by changing the angle of the projected light source 20 or the image projected by the light source 20 directly, or possibly moving a light guide (if present).

As indicated above, stereo ranging techniques can be used to control the adjustment of the light beam relative to the road surface. Thus, for any given pair of images which are acquired from the master and stereo cameras 14 and 16, the X displacement of a given feature, for example, the bright region(s) within the master inspection polygons, at a Y row in one image from the same feature in the other image indicates the range in metres of the Y row from the vehicle. Thus, knowing the range in metres of an illuminated object from the vehicle, the system 10 can therefore compensate for movement of the vehicle and so maintain the illuminated master inspection region at a distance of approximately 15 m from the vehicle as required by the relevant standards. It will be appreciated that this technique can be used to adjust with light beam on a frame-by-frame basis with a lag of as little as 1 image frame, but clearly some care needs to be taken when applying this approach to ensure that this lag does not cause the system to go out of control in for example, rough terrain. Thus, in some embodiments, rather than potentially adjusting the light source 20 every frame, the light source 20 could be adjusted say every minute during a measurement run.

It will be seen that in embodiments of the invention which include both left and right ranging cameras as well as the master camera 14, stereo ranging can also be performed as between a first of the left and right ranging cameras and the master camera 14 taking into account the relative angle between the two chosen cameras. This can be useful for measuring road markings imaged at very low angles.

Alternately, compensation could be achieved by measuring the angle of the light source 20 or camera 14, 16, 18 using the gyroscope 60, FIG. 1 and correcting this to the expected angle using a direct movement of the light source 20 or light guide (if present). This could be faster than the image processing based approach outlined above as it could be done continuously, perhaps using an analog circuit.

The above described embodiments have been described as inspecting a single traffic lane, with the system 10 being mounted on the front of a vehicle. Referring to FIG. 4(*c*), in a further variant, two lanes or separate lane markings could be inspected at the same time by incorporating a second system within an enclosure 12", calibrated accordingly and pointed to the other of a left or right hand lane than a first system. Thus such a system might comprise more than one illumination source 20(*a*), 20(*b*), each disposed below a respective master camera 14(*a*), 14(*b*). In this case, a stereo camera 16 is disposed between the master cameras 14(*a*), 14(*b*) and located above the horizontal plane of those cameras to provide an improved angle of incidence for ranging. In this case, the stereo camera 16 is used with master camera 14(*a*) for ranging road markings imaged on one side of the vehicle, while the stereo camera 16 is used with the other master camera 14(*b*) for ranging road markings imaged on the other side of the vehicle. Nonetheless, it will be appreciated than in variants of this embodiment, each master camera could act as a stereo camera for the other so avoiding the need for a separate stereo camera 16.

While embodiments of the invention have been described with reference to measuring the retroreflectivity of road markings such as lines and RPMs, variants of the embodiment can be employment for measuring the retroreflectivity of other retroreflective markers or signs (such as cat-eye's) placed on or along a road. The technique could be applied to the detection of road signs (and possible decoding of the sign for symbols and text).

While embodiments of the invention have been described with reference to a light source 20 substantially emitting in the whole or a large part of the green spectrum, the light source 20 could be arranged to emit light in a particular sub-portion of the green light spectrum. For example, the light source 20 could further comprise a green narrowband filter disposed between the one or the array of green LEDs and the aperture of the enclosure 12, so as to sharply narrow the spectrum of the green LED emitted light.

Accordingly, the first filter 201 applied by the master camera 14 would have a narrower bandpass substantially matching the bandpass of the filter associate with the light source 20. Applying a narrower green filter to the light received by the master camera 14 means rejecting more ambient light and, therefore, improve the accuracy of the retroreflectivity measurements.

While embodiments of the invention have been described with reference to a light source 20 comprising green LEDs, the light source 20 could be could be any of for example, an LCD projector, a DMD (Digital Micromirror Device) projector, a laser or some device capable of projecting light. An example of a suitable DMD projector is a Viewsonic Pro8500 and an example of a suitable LCD projector is a Hitachi CP-X3030WN.

It is noted that in some embodiments the light source 20 could be a white light source having one or more optical filters or masks associated thereto for allowing an emission of green light from the aperture of the enclosure 12.

Alternatively to the disclosed embodiments, the light source 20 could be arranged to project continuous light in a predetermined portion of the viewable light spectrum other than the green portion. Accordingly, the filters applied to incoming light in the master and stereo camera 14, 16 will have a bandpass matching such a predetermined portion, and the filter applied to incoming light in the reference camera 18 will have a bandpass matching at least one portion of the spectrum not including the particular spectrum portion of the emitted light.

While embodiments of the invention have been described with reference to a camera 18 applying a filter 202 having a bandpass matching the viewable red light spectrum, the filter 202 could have a bandpass matching, alternatively or in addition, portions of the infrared (IR) light spectrum, especially those closer to the viewable red light spectrum.

It will be appreciated that the inspection for identifying a road marking in a set of filtered images provided by the cameras 14, 16 and 18 can be performed on one of the filtered images provided by the reference camera 18 and the stereo camera 16, rather than from the filtered image provided by the master camera 14 as disclosed above.

While embodiments of the invention have been described with reference to a use of a single reference camera 18 selectively sensitive to red light, especially in night time conditions the system 10 can comprise a single colour reference camera having a Bayer filter whose red and blue channels can be used to provide separate red filtered and blue filtered images. This would provide the flexibility of using both red and blue intensity information to estimate $I_{Amb}$, where one of the blue and red intensities can be scaled, using for example calibration information available to the system 10, to be comparable with the other intensity. Furthermore, using a Bayer filter providing red and blue images would also allow the system 10 to discriminate between white and yellow road markings.

This reference colour camera could also be used to replace or integrate the master camera 14 or the stereo camera 16 in providing the green-filtered images, by using the green channel of the Bayer filter.

Alternatively, the reference camera 18 of the system can be a monochrome camera having a diachronic filter for providing magenta reference images.

It will be further appreciated that embodiments of the present invention can also operate in daylight and are not limited to working in night time conditions. Preferably, such embodiments require one or more of:

adding a second light source mounted in spatial relationship to the light source 20, e.g. as close as possible to the stereo camera 16, so as to illuminate each side of the traffic lane;

using a blue reference camera (indicated in FIGS. 4(*b*) and 4(*c*) with reference numerals 15; 15(*a*), 15*b* respectively) instead of or in addition to the red reference camera 18 (in the latter case, the red and blue master camera can be disposed in the enclosures 12',12" as close as possible and preferably at either side of the master camera(s) 14; 14(*a*), 14(*b*)). The grey level intensity data from each side could be scaled and added together.

Employing separate blue and red reference cameras allows the system 10 to very accurately estimate $I_{Amb}$, since both the blue and red intensity information are available (preferably scaled to be comparable to each other, e.g. using calibration information) while keeping sharp bandpass filtering for the blue and red portions of the light spectrum.

Embodiments of the present invention can be deployed for either day or night operation adjusting their operating parameters accordingly. For example, the exposure for the cameras 14-18 i.e. the gain level r exposure time, and the intensity for the illumination source(s) 20 can be controlled based on input from an ambient light sensor, to maintain an image signal coming from a retroreflective road marking such as a line as close to the camera sensor saturation level as possible, for example at approximately 200 grey levels out of a maximum of 255. As indicated, narrower filters on the cameras and illumination sources and providing them as close together as possible will have the effect of reducing the effective difference in raw pixel grey levels between day and night operation.

The invention claimed is:

1. A retroreflectivity measurement system comprising a structure arranged to be mounted to a front of a vehicle, the system comprising:

at least one light source mounted on said structure and arranged to project light across at least a portion of a traffic lane at a specified distance from the vehicle during a measurement run, the light being limited to a particular portion of the visible light spectrum;

a camera apparatus mounted on said structure in spaced apart relationship to said at least one light source and having a field of view including at least a portion of said traffic lane illuminated by said light source during said measurement run, the camera apparatus being selectively sensitive to light at said particular portion of the visible light spectrum to provide first filtered images of at least a portion of said illuminated portion of the traffic lane and said camera apparatus being separately selectively sensitive to light at least at one portion of the spectrum not including said particular portion to provide second filtered images of said illuminated portion of the traffic lane;

and a controller arranged to:
  a) obtain sequences of first and corresponding one or more second filtered images from said camera apparatus during said measurement run;
  b) identify within at least one of said sequences of images, at least a portion of a road marking illuminated by said light source;
  c) determine a first intensity of said at least a portion of the road marking from a first filtered image containing said at least a portion of the road marking;
  d) determine a further intensity of said at least a portion of the road marking from the corresponding one or more second filtered images;
  e) estimate an ambient intensity of said at least a portion of the road marking within said particular portion of the light spectrum, by applying a scaling factor to said further intensity; and
  f) determine a retroreflectivity of said at least a portion of the road marking as a function of said first intensity and said estimated ambient intensity including subtracting said estimated ambient intensity from said first intensity.

2. The system of claim 1, wherein the system is arranged to acquire through said camera apparatus said first and corresponding one or more second filtered images substantially at the same time.

3. The system of claim 1, wherein said camera apparatus is selectively sensitive to light at least at separated first and second portions of the light spectrum not including said particular portion to provide said second filtered images of said portion of the illuminated traffic lane.

4. The system of claim 3, wherein said controller is arranged to:

determine a second intensity of said at least a portion of the road marking from the corresponding second filtered image in the first portion of the light spectrum;

determine a third intensity of said at least a portion of the road marking from the corresponding second filtered image in the second portion of the light spectrum; and determine said further intensity of said at least a portion of the road marking from said second and third intensities.

5. The system of claim 1, wherein said particular portion of the light spectrum is limited to the green light spectrum.

6. The system of claim 5, wherein a peak illumination intensity of said light is substantially at a wavelength corresponding to the peak of the photopic response of the human eye.

7. The system of claim 1, wherein said camera apparatus comprises a single camera with a colour filter array.

8. The system of claim 1, wherein said controller is arranged to determine a distance from the vehicle of said at least a portion of the road marking, and wherein said retroreflectivity is determined as a function of said distance.

9. The system of claim 1, further including an interface to said vehicle, said controller being arranged to determine one or more of: said vehicle speed, distance travelled or headlight state via said interface.

10. The system of claim 3, wherein said first portion and said second portion of the light spectrum are limited to the red light spectrum and the blue light spectrum, respectively.

11. The system of claim 3, wherein said camera apparatus comprises at least a master camera arranged to provide said first filtered images and at least one reference camera arranged to provide said second filtered images.

12. The system of claim 11, wherein said at least one reference camera comprises at least a first reference camera and a second reference camera arranged to separately provide the second filtered images in said first portion and in said second portion, respectively, of the light spectrum.

13. The system of claim 12, wherein said first and second reference cameras are mounted on said structure at either side of said master camera.

14. The system of claim 11, wherein said system is arranged to acquire through said master camera and said at least one reference camera said first and corresponding one or more second filtered images at the same time.

15. A retroreflectivity measurement system comprising a structure arranged to be mounted to a front of a vehicle, the system comprising:
- at least one light source mounted on said structure and arranged to project light across at least a portion of a traffic lane at a specified distance from the vehicle during a measurement run, the light being limited to a particular portion of the visible light spectrum;
- a camera apparatus mounted on said structure in spaced apart relationship to said at least one light source and having a field of view including at least a portion of said traffic lane illuminated by said light source during said measurement run, the camera apparatus being selectively sensitive to light at said particular portion of the visible light spectrum to provide first filtered images of at least a portion of said illuminated portion of the traffic lane and said camera apparatus being separately selectively sensitive to light at least at separated first and second portions of the light spectrum not including said particular portion of the visible light spectrum to provide second filtered images of said illuminated portion of the traffic lane; and
- a controller arranged to:
  a) obtain sequences of first and corresponding one or more second filtered images from said camera apparatus during said measurement run;
  b) identify within at least one of said sequences of images, at least a portion of a road marking illuminated by said light source;
  c) determine a first intensity of said at least a portion of the road marking from a first filtered image containing said at least a portion of the road marking;
  d) determine a second intensity of said at least a portion of the road marking from the corresponding second filtered image in the first portion of the light spectrum;
  e) determine a third intensity of said at least a portion of the road marking from the corresponding second filtered image in the second portion of the light spectrum;
  f) determine a further intensity of said at least a portion of the road marking by averaging said second and third intensities;
  g) estimate an ambient intensity of said at least a portion of the road marking within said particular portion of the light spectrum, by applying a scaling factor to said further intensity; and
  h) determine a retroreflectivity of said at least a portion of the road marking as a function of said first intensity and said estimated ambient intensity.

16. The system of claim 15, wherein said controller is arranged to scale one of said second and third intensities before said averaging.

17. A retroreflectivity measurement system comprising a structure arranged to be mounted to a front of a vehicle, the system comprising:
- at least one light source mounted on said structure and arranged to project light across at least a portion of a traffic lane at a specified distance from the vehicle during a measurement run, the light being limited to a particular portion of the visible light spectrum;
- a camera apparatus mounted on said structure in spaced apart relationship to said at least one light source and having a field of view including at least a portion of said traffic lane illuminated by said light source during said measurement run, the camera apparatus comprising a master camera selectively sensitive to light at said particular portion of the visible light spectrum to provide first filtered images of at least a portion of said illuminated portion of the traffic lane and a single reference camera being selectively sensitive to light at least at separated first and second portions of the light spectrum not including said particular portion of the visible light spectrum to provide separate second filtered images in said first portion and in said second portion of the light spectrum of said illuminated portion of the traffic lane; and
- a controller arranged to:
  a) obtain sequences of first and corresponding second filtered images from said camera apparatus during said measurement run;
  b) identify within at least one of said sequences of images, at least a portion of a road marking illuminated by said light source;
  c) determine a first intensity of said at least a portion of the road marking from a first filtered image containing said at least a portion of the road marking;
  d) determine a further intensity of said at least a portion of the road marking from the corresponding second filtered images;
  e) estimate an ambient intensity of said at least a portion of the road marking within said particular portion of the light spectrum, by applying a scaling factor to said further intensity; and
  f) determine a retroreflectivity of said at least a portion of the road marking as a function of said first intensity and said estimated ambient intensity.

18. The system of claim 17, wherein said single reference camera comprises a colour filter array.

19. The system of claim 17, wherein said single reference camera is arranged to provide second filtered images each having component frequencies in both said first portion and said second portion of the light spectrum.

20. The system of claim 19, wherein said single reference camera comprises a magenta dichroic filter.

* * * * *